United States Patent
Okamoto et al.

(10) Patent No.: US 11,441,098 B2
(45) Date of Patent: Sep. 13, 2022

(54) α-HYDROXYISOBUTYRATE ESTER COMPOUND, FRAGRANCE COMPOSITION, AND USE THEREOF AS FRAGRANCE

(71) Applicant: MITSUBISHI GAS CHEMICAL COMPANY, INC., Chiyoda-ku (JP)

(72) Inventors: Atsushi Okamoto, Niigata (JP); Eriko Kushida, Niigata (JP); Umi Yokobori, Niigata (JP); Kyoko Kimura, Niigata (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 0 days.

(21) Appl. No.: 17/255,093

(22) PCT Filed: Jun. 26, 2019

(86) PCT No.: PCT/JP2019/025396
§ 371 (c)(1),
(2) Date: Dec. 22, 2020

(87) PCT Pub. No.: WO2020/004468
PCT Pub. Date: Jan. 2, 2020

(65) Prior Publication Data
US 2021/0269740 A1  Sep. 2, 2021

(30) Foreign Application Priority Data
Jun. 26, 2018 (JP) ............... JP2018-121112

(51) Int. Cl.
*C11B 9/00* (2006.01)
*C07C 69/675* (2006.01)

(52) U.S. Cl.
CPC .......... *C11B 9/0019* (2013.01); *C07C 69/675* (2013.01)

(58) Field of Classification Search
CPC ...... C11B 9/0019; C07C 69/675; C07C 59/00
See application file for complete search history.

(56) References Cited

U.S. PATENT DOCUMENTS

| 1,775,636 A | * | 9/1930 | Bogin ............. C07C 59/00 560/179 |
| 2,836,611 A | | 5/1958 | Exner et al. |
| 3,368,943 A | | 2/1968 | Gilbert et al. |
| 3,959,396 A | * | 5/1976 | Ochsner ............ C11B 9/0015 568/903 |
| 5,612,303 A | * | 3/1997 | Takayanagi ........ C09J 11/06 134/40 |
| 6,322,838 B1 | | 11/2001 | Güntert et al. |

FOREIGN PATENT DOCUMENTS

| CH | 689 620 A5 | 7/1999 |
| JP | 7-228895 A | 8/1995 |

OTHER PUBLICATIONS

Welke, et al., Characterization of the volatile profile of Brazilian Merlot wines through comprehensive two dimensional gas chromatography time-of-flight mass spectrometric detection, Journal of Chromatography A, vol. 1226, pp. 124-139 (Year: 2012).*
International Search Report dated Aug. 27, 2019 in PCT/JP2019/025396 filed Jun. 26, 2019, citing documents AA-AB and AW-AY therein, 2 pages.
Welke, J., et al., "Characterization of the volatile profile of Brazilian Merlot wines through comprehensive two dimensional gas chromatography time-of-flight mass spectrometric detection", Journal of Chromatography A, vol. 1226, 2012, pp. 124-139.
Venskutonis, P.R., et al., "Flavour composition of some-lemon-like aroma herbs from Lithuania", Developments in Food Science, vol. 37, 1995, pp. 833-847.
Zemlicka, L., et al., "Analysis of natural aroma and flavor of MD2 pineapple variety", Acta Chemica Slovaca, vol. 6, No. 1, 2013, pp. 123-128.
Koryo, G., et al., "Synthetic fragrance: chemistry and product knowledge, new enlarged edition", The Chemical Daily Co. Ltd., 2016, pp. 580-582 (total 4 pages).

* cited by examiner

*Primary Examiner* — Yate' K Cutliff
(74) *Attorney, Agent, or Firm* — Oblon, McClelland, Maier & Neustadt, L.L.P.

(57) ABSTRACT

A fragrance composition comprising a compound represented by Formula (1): wherein, in Formula (1), R represents a linear, branched, or cyclic alkyl group having 2 to 6 carbon atoms.

(1)

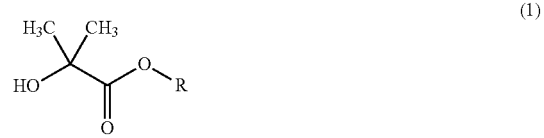

3 Claims, No Drawings

α-HYDROXYISOBUTYRATE ESTER COMPOUND, FRAGRANCE COMPOSITION, AND USE THEREOF AS FRAGRANCE

TECHNICAL FIELD

The present invention relates to α-hydroxyisobutyrate ester compounds, fragrance compositions, and uses thereof as fragrances.

BACKGROUND ART

Some isobutyric esters are known to be compounds useful as fragrances. For example, Non Patent Document 1 describes that various isobutyric esters are mainly used as flavors, and all these isobutyric esters are flavor materials having a fruit scent; specifically, methyl isobutyrate gives a sweet apricot-like scent, propyl isobutyrate gives a strong pineapple-like scent, butyl isobutyrate gives a fresh apple- and banana-like scent, and isoamyl isobutyrate gives a sweet apricot- and pineapple-like scent.

Additionally, Patent Document 1 discloses that, as an isobutyric ester having a bond with oxygen at the α-position, a linear or branched alkyl ester having 4 to 12 carbon atoms of α-alkoxyisobutyric acid is useful as a fragrance, and n-hexyl α-ethoxyisobutyrate has a lavender-like aroma.

On the other hand, many of α-hydroxyisobutyrate esters are known substances.

For example, Patent Document 2 discloses that n-propyl, isopropyl, n-butyl, isobutyl, and amyl esters of α-hydroxyisobutyric acid are solvents having excellent dissolvability for nitrocellulose.

Furthermore, Patent Document 3 discloses that ethyl, isopropyl, and butyl esters of α-hydroxyisobutyric acid are useful as low-toxic and highly-safe solvents for degreasing cleaning agents, flux cleaning agents, resist stripping agents, and the like.

CITATION LIST

Patent Documents

Patent Document 1: U.S. Pat. No. 3,368,943
Patent Document 2: U.S. Pat. No. 1,775,636
Patent Document 3: JP H07-228895 A

Non Patent Document

Non-Patent Document 1: "Gousei Koryo: Kagaku to Shohin Chishiki, zoho shinban (Synthetic fragrance: chemistry and product knowledge, new enlarged edition)", The Chemical Daily Co. Ltd., 2016, pp. 580 to 582

DISCLOSURE OF THE INVENTION

Technical Problem

An object to be solved by the present invention is to provide an α-hydroxyisobutyrate ester compound, useful as a fragrance and a fragrance ingredient. Further, another object to be solved by the present invention is to provide a fragrance composition containing an α-hydroxyisobutyrate ester compound as an active ingredient and use of the compound as a fragrance.

Solution to Problem

The present inventors have synthesized various compounds and have made diligent research of the aromas thereof. Thus, the present inventors discovered that particular ester compounds of α-hydroxyisobutyric acid are useful as fragrances and fragrance ingredients.

That is, the present invention is as follows.

<1> A fragrance composition comprising a compound represented by Formula (1) as an active ingredient:

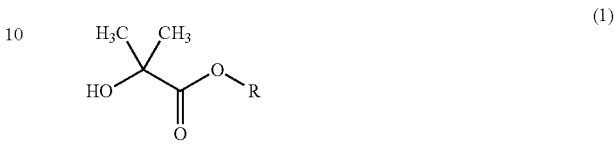

wherein, in Formula (1), R represents a linear, branched, or cyclic alkyl group having 2 to 6 carbon atoms.

<2> The fragrance composition according to <1>, wherein, in Formula (1), R is selected from the group consisting of an ethyl group, a n-propyl group, an isopropyl group, a n-butyl group, an isobutyl group, a sec-butyl group, a tert-butyl group, a 3-methylbutan-2-yl group, a 2-methylbutyl group, a 3-methylbutyl group, a neopentyl group, a 2-methylpentyl group, 4-methylpentan-2-yl group, a n-hexyl group, a cyclopentyl group, and a cyclohexyl group.

<3> Use of a compound represented by Formula (1) as a fragrance:

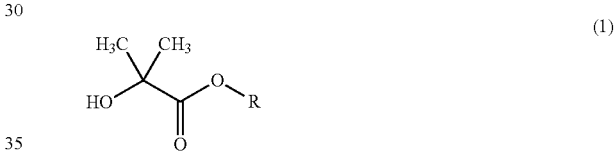

wherein, in Formula (1), R represents a linear, branched, or cyclic alkyl group having 2 to 6 carbon atoms.

<4> The use according to <3>, wherein, in Formula (1), R is selected from the group consisting of an ethyl group, a n-propyl group, an isopropyl group, a n-butyl group, an isobutyl group, a sec-butyl group, a tert-butyl group, a 3-methylbutan-2-yl group, a 2-methylbutyl group, a 3-methylbutyl group, a neopentyl group, a 2-methylpentyl group, a 4-methylpentan-2-yl group, a n-hexyl group, a cyclopentyl group, and a cyclohexyl group.

<5> The use according to <3> or <4>, wherein the compound represented by Formula (1) imparts a mint-like scent.

<6> The use according to <3> or <4>, wherein the compound represented by Formula (1) imparts a green-note scent.

<7> The use according to <3> or <4>, wherein the compound represented by Formula (1) imparts a fruity-note scent.

<8> A compound, represented by Formula (2) below:

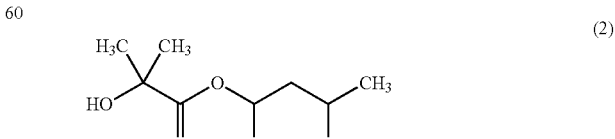

Advantageous Effects of Invention

According to the present invention, it is possible to provide an α-hydroxyisobutyrate ester compound, useful as a fragrance and a fragrance ingredient. Further, according to the present invention, it is possible to provide a fragrance composition containing an α-hydroxyisobutyrate ester compound as an active ingredient and use of the compound as a fragrance.

DESCRIPTION OF EMBODIMENTS

[Fragrance Composition and Use]

A fragrance composition of the present invention comprises a compound represented by Formula (1) below as an active ingredient. Furthermore, use of the present invention is use of the compound represented by Formula (1) below as a fragrance. So far, α-hydroxyisobutyrate ester compounds have been reported, but no related documents have described scents specific to α-hydroxyisobutyrate esters.

The present invention will be described in detail hereinbelow.

<Compound Represented by Formula (1)>

The compound to be used in the fragrance composition of the present invention and the use of the present invention is represented by Formula (1) below:

$$\underset{\text{HO}}{\overset{\text{H}_3\text{C}\quad\text{CH}_3}{\diagup}}\!\!\!\!\diagdown\!\!\!\!\underset{\text{O}}{\overset{}{\text{C}}}\!\!-\!\!\text{O}\!-\!\text{R} \tag{1}$$

wherein, in Formula (1), R represents a linear, branched, or cyclic alkyl group having 2 to 6 carbon atoms.

In Formula (1), specific examples of R include an ethyl group, a n-propyl group, an isopropyl group, a n-butyl group, an isobutyl group (2-methylpropyl group), a sec-butyl group (1-methylpropyl group), a tert-butyl group, a n-pentyl group, a 1-methylbutyl group (2-pentyl group), a 2-methylbutyl group, a 3-methylbutyl group, a neopentyl group (2,2-dimethylpropyl group), a 2-methylbutan-2-yl group, a 1-ethylpropyl group (3-pentyl group), a 3-methylbutan-2-yl group, a n-hexyl group, a 1-methylpentyl group (2-hexyl group), a 2-methylpentyl group, a 3-methylpentyl group, a 4-methylpentyl group, a 2-methylpentan-2-yl group, a 2,2-dimethylbutyl group, a 3,3-dimethylbutyl group, a 3-methylpentan-2-yl group, a 2,3-dimethylbutyl group, a 4-methylpentan-2-yl group, a 3-hexyl group, a 2-ethylbutyl group, a 2,3-dimethylbutan-2-yl group, a 3,3-dimethylbutan-2-yl group, a 4-methylpentan-3-yl group, a cyclopropyl group, a cyclobutyl group, a cyclopentyl group, and a cyclohexyl group. Among these, from the perspective of having a mint-like aroma, a floral aroma, a green-note aroma, or a fruity-note aroma, R is preferably a group selected from the group consisting of an ethyl group, a n-propyl group, an isopropyl group, a n-butyl group, an isobutyl group, a sec-butyl group, a tert-butyl group, a 3-methylbutan-2-yl group, a 2-methylbutyl group, a 3-methylbutyl group, a neopentyl group, a 2-methylpentyl group, a 4-methylpentan-2-yl group, a n-hexyl group, a cyclopentyl group, and a cyclohexyl group. Additionally, from the perspective of having a mint-like aroma, R is also preferably a group selected from the group consisting of an ethyl group, a n-propyl group, an isopropyl group, a n-butyl group, an isobutyl group, a 2-methylbutyl group, a 3-methylbutyl group, a 4-methylpentan-2-yl group, a cyclopentyl group, and a cyclohexyl group.

When the R group has one or more asymmetric carbons, the compound represented by Formula (1) comprises any one of optical isomers resulting from the asymmetric carbon or a mixture of the isomers at any proportion.

The compound represented by Formula (1), which is useful as a fragrance and a fragrance ingredient, has a mint-like aroma as well as simultaneously exhibits an aroma of a woody tone, spicy tone, floral tone, green tone, or the like due to the difference in the alkyl groups (R) of the ester moiety. In addition, some of the compounds represented by Formula (1) above have a green-note aroma or a fruity-note aroma. Such compounds are useful as a fragrance and a fragrance ingredient, also in this respect.

Particularly preferably, R is an ethyl group.
Particularly preferably, R is a n-propyl group.
Particularly preferably, R is an isopropyl group.
Particularly preferably, R is a n-butyl group.
Particularly preferably, R is an isobutyl group.
Particularly preferably, R is a sec-butyl group.
Particularly preferably, R is a tert-butyl group.
Particularly preferably, R is a 3-methylbutan-2-yl group.
Particularly preferably, R is a 2-methylbutyl group.
Particularly preferably, R is a 3-methylbutyl group.
Particularly preferably, R is a neopentyl group.
Particularly preferably, R is a 2-methylpentyl group.
Particularly preferably, R is a 4-methylpentan-2-yl group.
Particularly preferably, R is a n-hexyl group.
Particularly preferably, R is a cyclopentyl group.
Particularly preferably, R is a cyclohexyl group.

In the present invention, examples of the compound represented by Formula (1) include compounds represented by any of Formulas (1-1) to (1-35) below. Preferred compounds are compounds represented by any of Formulas (1-1) to (1-10), (1-13), (1-16) to (1-18), (1-21), and (1-24) below, and preferable compounds are compounds represented by any of Formulas (1-1) to (1-10) below:

$$\underset{\text{HO}}{\overset{\text{H}_3\text{C}\quad\text{CH}_3}{\diagup}}\!\!\!\!\diagdown\!\!\!\!\underset{\text{O}}{\overset{}{\text{C}}}\!\!-\!\!\text{O}\!-\!\text{CH}_3 \tag{1-1}$$

$$\underset{\text{HO}}{\overset{\text{H}_3\text{C}\quad\text{CH}_3}{\diagup}}\!\!\!\!\diagdown\!\!\!\!\underset{\text{O}}{\overset{}{\text{C}}}\!\!-\!\!\text{O}\!-\!\text{CH}_2\text{CH}_3 \tag{1-2}$$

$$\underset{\text{HO}}{\overset{\text{H}_3\text{C}\quad\text{CH}_3}{\diagup}}\!\!\!\!\diagdown\!\!\!\!\underset{\text{O}}{\overset{}{\text{C}}}\!\!-\!\!\text{O}\!-\!\text{CH(CH}_3)_2 \tag{1-3}$$

$$\underset{\text{HO}}{\overset{\text{H}_3\text{C}\quad\text{CH}_3}{\diagup}}\!\!\!\!\diagdown\!\!\!\!\underset{\text{O}}{\overset{}{\text{C}}}\!\!-\!\!\text{O}\!-\!\text{CH}_2\text{CH}_2\text{CH}_3 \tag{1-4}$$

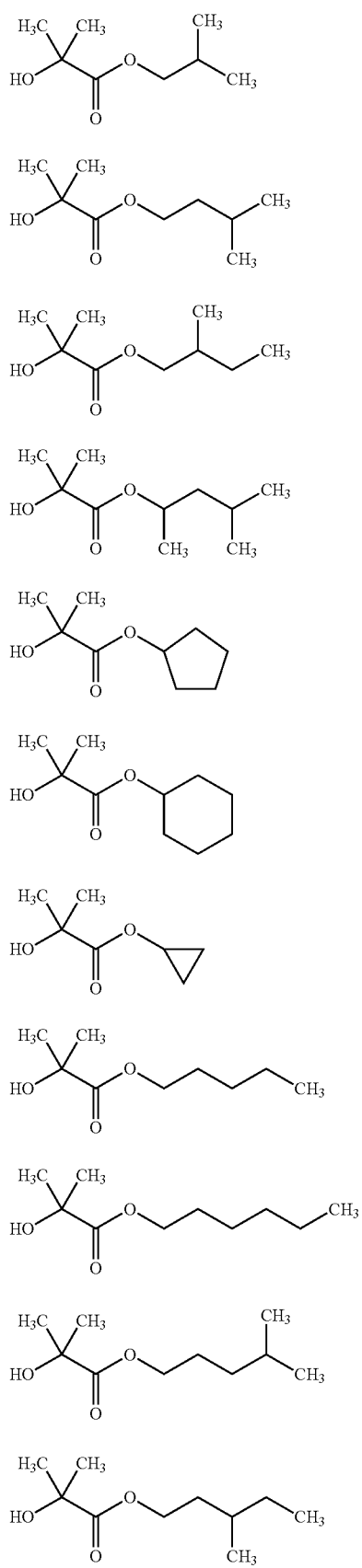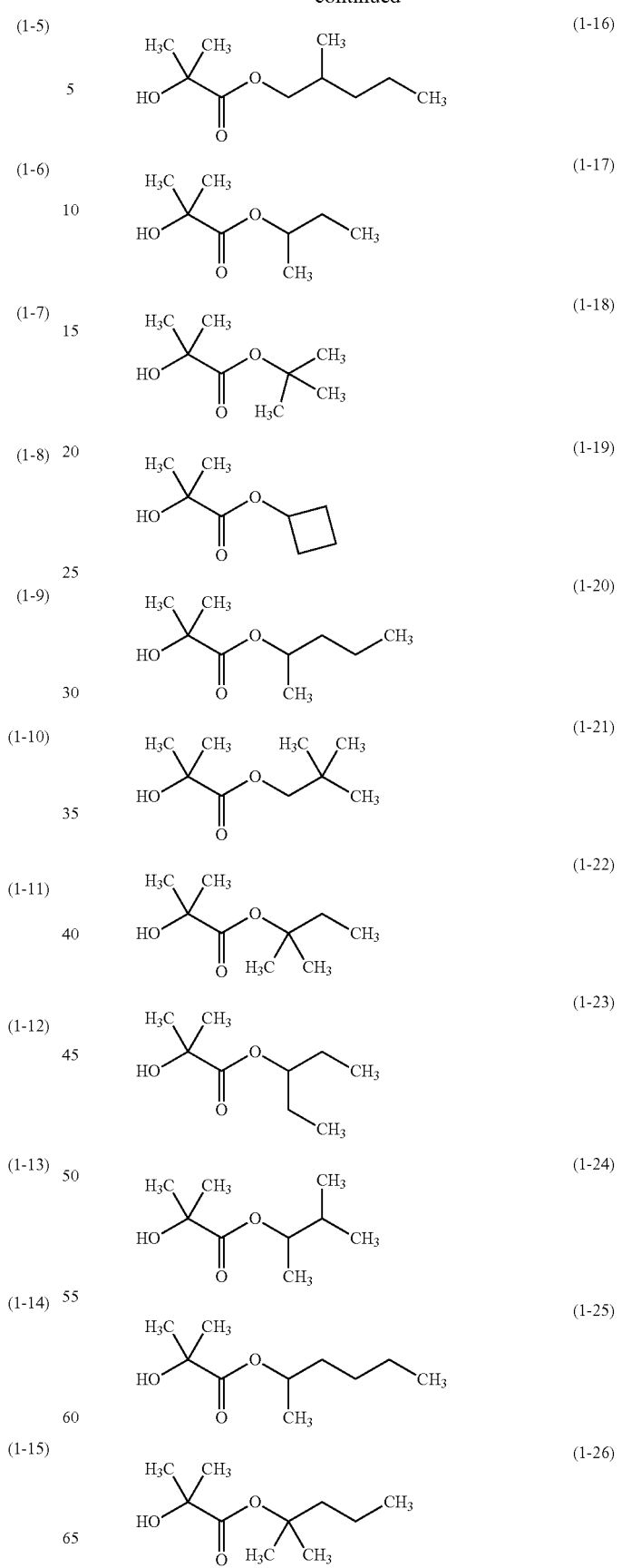

-continued

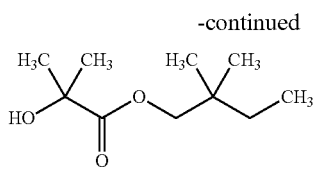
(1-27)

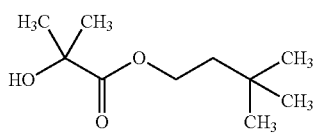
(1-28)

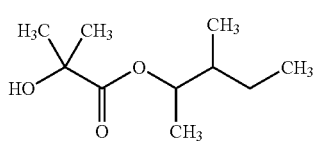
(1-29)

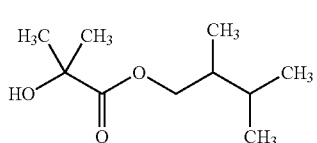
(1-30)

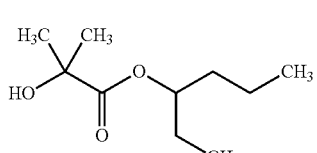
(1-31)

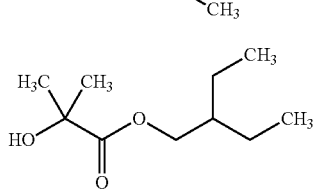
(1-32)

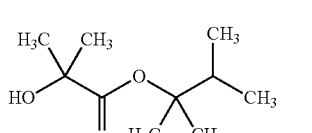
(1-33)

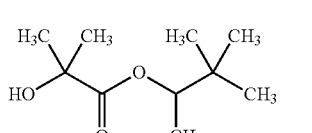
(1-34)

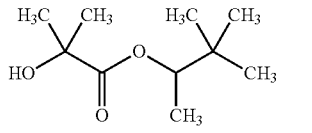
(1-35)

In recent years, there is a trend to focus more on the toxicity and environmental impact of chemicals, and fragrances or fragrance compositions are no exception. There is an increase in the number of cases where a fragrance which has been used in the past is severely restricted in usage conditions or is prohibited from use due to their sensitization properties to a human body, tendency to accumulate in the environment, and the like. Thus, there is a strong demand for a fragrance and a fragrance composition having a lower environmental impact. Accordingly, fragrance ingredients also preferably have excellent biodegradability and show a low degree of bioaccumulation.

The compound represented by Formula (1) contains a compound excellent in biodegradability and showing a low degree of bioaccumulation, and from this perspective, R is preferably a group selected from the group consisting of an ethyl group, a n-propyl group, an isopropyl group, a n-butyl group, an isobutyl group, a sec-butyl group, a tert-butyl group, a 3-methylbutan-2-yl group, a 2-methylbutyl group, a 3-methylbutyl group, a neopentyl group, a 2-methylpentyl group, a 4-methylpentan-2-yl group, a n-hexyl group, a cyclopentyl group, and a cyclohexyl group. Additionally, from the same perspective, R is preferably a group selected from the group consisting of an ethyl group, a n-propyl group, an isopropyl group, a n-butyl group, an isobutyl group, a 2-methylbutyl group, a 3-methylbutyl group, a 4-methylpentan-2-yl group, a cyclopentyl group, and a cyclohexyl group.

The compound represented by Formula (1) is useful as a fragrance because the compound has an excellent aroma as described below. Generally, a fragrance is rarely used alone, and often used in a fragrance compound (fragrance composition) produced by compounding a plurality of fragrances in accordance with the purpose. The compound represented by Formula (1) is useful as a fragrance (also called a "fragrance ingredient") to be blended in a fragrance compound (fragrance composition), and the fragrance composition of the present invention contains the compound represented by Formula (1) as an active ingredient. As the fragrance, one of the compounds represented by Formula (1) above may be used alone or two or more of the compounds may be used in combination.

Additionally, the compound represented by Formula (1) may include a small amount of impurities, by-products, contaminants, and the like as long as the effects of the present invention are not compromised.

The compound represented by Formula (1) has a mint-like aroma as well as an aroma of woody-tone, spicy-tone, floral-tone, green-tone, or like, and also is excellent in diffusivity. In addition, some of the compounds represented by Formula (1) above have a green-note aroma or a fruity-note aroma and also are excellent in diffusivity. The compound represented by Formula (1) may be used alone as a fragrance and added to various perfumery and cosmetics, healthcare and sanitary materials as well as medicinal supplies, household goods, foods, and the like to thereby impart an aroma thereto. Alternatively, the compound represented by Formula (1) may be mixed with another fragrance ingredient or the like to prepare a fragrance composition (fragrance compound) described below, which may be blended into a variety of products to impart an aroma. Among these, from the perspective of obtaining an intended aroma, it is preferred that the compound represented by Formula (1) be blended in a fragrance composition as a fragrance ingredient to prepare a fragrance composition containing the compound represented by Formula (1) as an active ingredient and the fragrance composition be blended in a product to perfume the product.

Additionally, the compound represented by Formula (1) is preferably used as a fragrance and is more preferably used to impart a mint-like scent, a green-note scent, or a fruity-note scent.

<Fragrance Composition>

The fragrance composition (fragrance compound) of the present invention contains the compound represented by Formula (1) as an active ingredient. Note that the fragrance composition is not particularly limited as long as that it contains at least one compound represented by Formula (1), and two or more compounds represented by Formula (1) may be included.

The fragrance composition according to an embodiment of the present invention is only required to contain the compound represented by Formula (1) as an active ingredient, and other ingredients are not particularly limited. However, the fragrance composition preferably contains another fragrance ingredient (hereinafter, also referred to as a "known fragrance").

Note that the "fragrance composition (fragrance compound)" is a composition that is added to various perfumery and cosmetics, medicinal supplies, foods, beverages, and the like to impart an aroma thereto, or a composition that is used as it is in a perfume or the like. The fragrance composition may contain an additive such as a solvent, as required, in addition to the known fragrance.

The amount of the compound represented by Formula (1) blended depends on the type of the compound, the type of aroma intended, the intensity of the aroma, and the like. The amount of the compound represented by Formula (1) in the fragrance composition is preferably 0.001 mass % or greater, more preferably 0.01 mass % or greater, and even more preferably 0.1 mass % or more, and preferably 90 mass % or less, more preferably 70 mass % or less, and even more preferably 50 mass % or less.

The known fragrance is not particularly limited as long as it is a known fragrance component, and a wide range of fragrances can be used. For example, one or two or more of the following fragrances can be selected and used at any mixing ratio.

Examples thereof include hydrocarbons such as limonene, α-pinene, β-pinene, terpinene, cedrene, longifolene, and valencene; alcohols such as linalool, citronellol, geraniol, nerol, terpineol, dihydromyrcenol, ethyllinalool, farnesol, nerolidol, cis-3-hexenol, cedrol, menthol, borneol, β-phenylethyl alcohol, benzyl alcohol, phenyl hexanol, 2,2,6-trimethylcyclohexyl-3-hexanol, 1-(2-t-butylcyclohexyloxy)-2-butanol, 4-isopropylcyclohexane methanol, 4-t-butylcyclohexanol, 4-methyl-2-(2-methylpropyl)tetrahydro-2H-pyran-4-ol, 2-methyl-4-(2,2,3-trimethyl-3-cyclopenten-1-yl)-2-butene-1-ol, 2-ethyl-4-(2,2,3-trimethyl-3-cyclopenten-1-yl)-2-buten-1-ol, isocamphylcyclohexanol, and 3,7-dimethyl-7-methoxyoctane-2-ol; phenols such as eugenol, thymol, and vanillin; esters such as linalyl formate, citronellyl formate, geranyl formate, n-hexyl acetate, cis-3-hexenyl acetate, linalyl acetate, citronellyl acetate, geranyl acetate, neryl acetate, terpinyl acetate, nopyl acetate, bornyl acetate, isobronyl acetate, o-t-butylcyclohexyl acetate, p-t-butylcyclohexyl acetate, tricyclodecenyl acetate, benzyl acetate, styralyl acetate, cinnamyl acetate, dimethylbenzylcarbinyl acetate, 3-pentyltetrahydropyran-4-yl acetate, citronellyl propionate, tricyclodecenyl propionate, allylcyclohexyl propionate, ethyl-2-cyclohexyl propionate, benzyl propionate, citronellyl butyrate, dimethylbenzylcarbinyl n-butyrate, tricyclodecenyl isobutyrate, methyl-2-nonenoate, methyl benzoate, benzyl benzoate, methyl cinnamate, methyl salicylate, n-hexyl salicylate, cis-3-hexenyl salicylate, geranyl tiglate, cis-3-hexenyl tiglate, methyl jasmonate, methyldihydro jasmonate, methyl-2,4-dihydroxy-3,6-dimethyl benzoate, ethylmethylphenyl glycidate, methyl anthranilate, and FRUITATE; aldehydes such as n-octanal, n-decanal, n-dodecanal, 2-methylundecanal, 10-undecenal, citronellal, citral, hydroxycitronellal, dimethyl tetrahydrobenzaldehyde, 4(3)-(4-hydroxy-4-methylpentyl)-3-cyclohexene-1-carboaldehyde, 2-cyclohexyl propanal, p-t-butyl-α-methylhydrocinnamic aldehyde, p-isopropyl-α-methylhydrocinnamic aldehyde, p-ethyl-α,α-dimethylhydrocinnamic aldehyde, α-amylcinnamic aldehyde, α-hexylcinnamic aldehyde, piperonal, and α-methyl-3,4-methylenedioxyhydrocinnamic aldehyde; ketones such as methylheptenone, 4-methylene-3,5,6,6-tetramethyl-2-heptanone, amylcyclopentanone, 3-methyl-2-(cis-2-pentene-1-yl)-2-cyclopentene-1-on, methylcyclopentenolone, rose ketones, γ-methylionone, α-ionone, carbone, menthone, camphor, nootkatone, benzylacetone, anisylacetone, methyl-β-naphthylketone, 2,5-dimethyl-4-hydroxy-3(2H)-furanone, maltol, 7-acetyl-1,2,3,4,5,6,7,8-octahydro-1,1,6,7-tetramethyl naphthalene, muscone, civetone, cyclopentadecanone, and cyclohexedecanone; acetals and ketals such as acetoaldehyde ethylphenylpropyl acetal, citraldiethyl acetal, phenylacetoaldehyde glycerin acetal, and ethylacetoacetate ethyleneglycol ketals; ethers such as anethole, β-naphthylmethyl ether, β-naphthylethyl ether, limonene oxide, rose oxide, 1,8-cineol, and racemic or photoactive dodecahydro-3a,6,6,9a-tetramethylnaphtho[2,1-b]furane; nitriles such as citronellyl nitrile; lactones such as γ-nonalactone, γ-undecalactone, σ-decalactone, γ-jasmolactone, coumarin, cyclopentadecanolide, cyclohexadecanolide, ambrettolide, ethylene brassylate, and 11-oxahexadecanolide; natural essential oils and natural extracts of orange, lemon, bergamot, mandarin, peppermint, spearmint, lavender, chamomile, rosemary, eucalyptus, sage, basil, rose, geranium, jasmine, ylang-ylang, anise, clove, ginger, nutmeg, cardamom, cedar, Japanese cypress, sandalwood, vetiver, patchouli, and labdanum; and other fragrance materials such as synthetic fragrances.

In addition, the fragrance composition may also contain, as components besides the fragrance ingredients, a surfactant such as polyoxyethylene lauryl sulfate ether; a solvent such as dipropylene glycol, diethyl phthalate, ethylene glycol, propylene glycol, methyl myristate, triethyl citrate, or the like; an antioxidant; a coloring agent, and the like.

The compound represented by Formula (1), which has a mint-like aroma and simultaneously has an aroma of a woody tone, a spicy tone, a floral tone, a green tone, or the like, can impart a natural woody tone, a spicy tone, a floral tone, or green tone in addition to the mint tone when combined with a known fragrance. Thus, the compound is usefully added to various perfumery and cosmetics, healthcare and sanitary materials as well as to medicinal supplies, household goods, foods, and the like to thereby impart an aroma thereto.

Examples of products to which a fragrance composition containing the compound represented by Formula (1) can be added to impart an aroma and improve the aroma of the blend object include various products such as perfumery and cosmetics, health and sanitary materials, miscellaneous goods, beverages, foods, quasi-pharmaceutical products, and medicinal supplies; the fragrance composition can be used as an aroma component in, for example, fragrance products such as perfumes and colognes; hair cosmetics such as shampoos, rinses, hair tonics, hair creams, mousses, gels, pomades, sprays, and the like; skin cosmetics such as skin lotions, essences, creams, milky lotions, packs, foundations, face powders, lipsticks, and various make-up products; various health and sanitary detergents such as dish washing detergents, laundry detergents, softeners, disinfecting detergents, anti-odor detergents, indoor fragrances, furniture cares, glass cleaners, furniture cleaners, floor cleaners, disinfectants, insecticides, bleaching agents, bactericides, repellants, and the like; quasi-pharmaceutical products such as toothpastes, mouthwashes, bath additives, antiperspirant products, and perming liquids; miscellaneous goods such as toilet paper and tissue paper; medicinal supplies; foods, and the like.

The amount of the fragrance composition blended in the product is not particularly limited, and the amount of the fragrance composition blended can be selected over a wide range, depending on the type, nature, and sensory benefits of the product to be perfumed. For example, the amount may be 0.00001 mass % or greater, preferably 0.0001 mass % or greater, and more preferably 0.001 mass % or greater. In the case of a fragrance such as perfume or the like, for example, the amount may be 100 mass %, preferably 80 mass % or less, more preferably 60 mass % or less, and even more preferably 40 mass % or less.

[Compound Represented by Formula (2)]

The compound represented by Formula (2) below is 4-methylpentan-2-yl 2-hydroxy-2-methyl propionate.

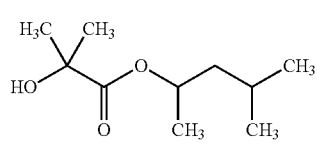

(2)

4-Methylpentan-2-yl 2-hydroxy-2-methylpropionate, represented by Formula (2), is a novel material. This compound, which has one asymmetric carbon, has two optical isomers and contains either one of them or a mixture thereof at any proportion.

4-Methylpentan-2-yl 2-hydroxy-2-methylpropionate is useful alone as a fragrance and is also useful as an active ingredient of fragrance compositions.

Additionally, 4-methylpentan-2-yl 2-hydroxy-2-methylpropionate is preferably used as a fragrance and is more preferably used to impart a mint-like scent.

[Method for Producing Compound Represented by Formula (1)]

The production method of the compound represented by Formula (1) is not particularly limited and may be appropriately selected from known methods and used.

For example, an α-hydroxyisobutyrate ester can be produced by subjecting a pyruvic ester and methyl halogenated magnesium to a Grignard reaction. The reaction formula for this reaction is shown as Formula (3) below.

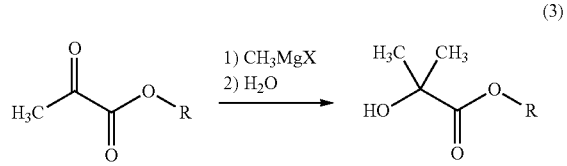

(3)

In Formula (3), R represents a linear, branched, or cyclic alkyl group having 2 to 6 carbon atoms. X represents a halogen element such as chlorine, bromine, iodine, or the like.

Alternatively, an α-hydroxyisobutyrate ester can be produced by esterifying α-hydroxyisobutyric acid with an alcohol in the presence of a catalyst. The reaction formula for this reaction is shown as Formula (4) below.

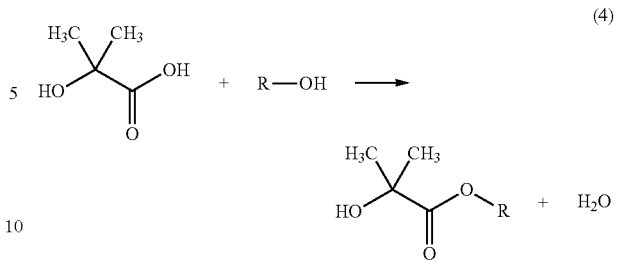

(4)

In Formula (4), R represents a linear, branched, or cyclic alkyl group having 2 to 6 carbon atoms.

Further, a target α-hydroxyisobutyrate ester can be produced by transesterifying an α-hydroxyisobutyrate ester with an alcohol of different kinds in the presence of a catalyst. The reaction formula for this reaction is shown as Formula (5) below.

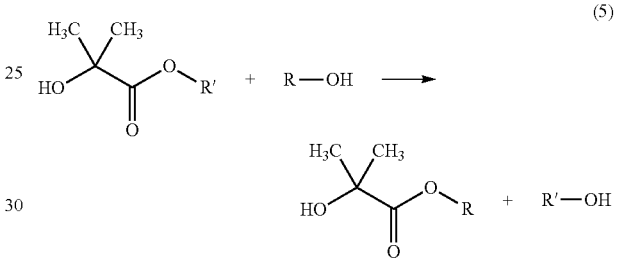

(5)

In Formula (5), R represents a linear, branched, or cyclic alkyl group having from 2 to 6 carbon atoms. R' is not particularly limited as long as it is an alkyl group different from R.

Known catalysts, reaction methods, reaction conditions, and reaction apparatus can be used as the catalyst, reaction method, reaction conditions, reaction apparatus, and the like to be used for these reactions, and there are no particular limitation thereon. In addition, as a method for purifying the obtained compound of Formula (1), a known purification method can be used, and there is no limitation thereon.

EXAMPLES

Hereinafter, the present invention will be described in further detail with reference to examples, but the present invention is not limited to these examples.

The reaction performance was evaluated according to the following expression.

Reaction yield (%)=[(number of moles of product ester in reaction solution)/(number of moles of raw material ester in solution fed)]×100%

<Gas Chromatography (GC) Analysis Conditions>

Apparatus: GC-2010 (available from Shimadzu Corporation, trade name)

Detector: FID

Column: DB-1 (capillary column available from J&W Scientific, Inc., trade name) (0.25 mmφ×60 m×0.25 μm)

<NMR Spectrum Analysis>

Identification of the ester was performed by $^1$H-NMR measurement and $^{13}$C-NMR measurement. The measurement conditions are shown below.

Apparatus: ECA500 (available from JEOL Ltd., trade name)

[¹H-NMR]

Nuclide: ¹H

Measurement frequency: 500 MHz

Measurement sample: 5% $CDCl_3$ solution

[¹³C-NMR]

Nuclide: ¹³C

Measurement frequency: 125 MHz

Measurement sample: 5% $CDCl_3$ solution

<Gas Chromatograph-Mass Spectrometry (GC-MS Analysis)>

Identification of the compounds was also performed by determining the molecular weight by GC-MS measurement (chemical ionization method [CI+], high resolution mass spectrometry [millimass]). The measurement conditions are shown below.

GC apparatus: Agilent 7890A (available from Agilent Technologies, trade name)

GC Measurement Conditions

Column: DB-1 (capillary column available from J&W Scientific, Inc., trade name) (0.25 mmφ×30 m×0.25 µm)

MS apparatus: JMS-T100GCV (available from JEOL Ltd., trade name)

MS measurement conditions: chemical ionization method

Detector conditions: 200 eV, 300 µA

Reagent gas: isobutane

The exact mass values of fragments detected in the protonated state by the chemical ionization method and the chemical composition formula thus attributed were described.

Example 1: Synthesis of Ethyl α-Hydroxyisobutyrate

In a 300 mL glass flask equipped with a distillation tube, 56.7 g of methyl α-hydroxyisobutyrate (available from Mitsubishi Gas Chemical Company, Inc.), 33.2 g of ethanol (available from Wako Pure Chemical Industries, Ltd.), and 0.92 g of titanium tetraethoxide (available from Wako Pure Chemical Industries, Ltd.) were loaded. A transesterification reaction was performed under normal pressure with heating and refluxing. The reaction was performed for 96 hours while methanol produced was extracted out of the system. As a result, ethyl α-hydroxyisobutyrate was obtained at a reaction yield of 97% by the reaction of Formula (6) below. After water was added to the reaction system to deactivate the catalyst, distillation was performed under reduced pressure to obtain 46.9 g of ethyl α-hydroxyisobutyrate (purity by GC analysis (hereinafter, also referred to as GC purity): 99.6%) as the fraction at 71 mmHg and 77° C.

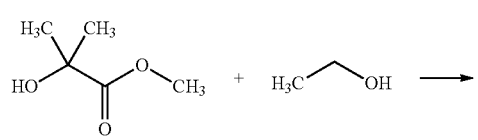

(6)

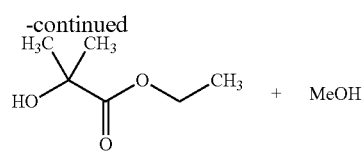

+ MeOH

Examples 2 to 13: Synthesis of Various α-Hydroxyisobutyrate Esters

Using the same reaction apparatus as in Reference Example 1, an appropriate amount of methyl α-hydroxyisobutyrate (available from Mitsubishi Gas Chemical Company, Inc.) was transesterified with a different alcohol (n-propanol, isopropanol, n-butanol, isobutanol, sec-butanol, 2-methylbutanol, neopentyl alcohol, 2-methylpentanol, n-hexanol, cyclopentanol, cyclohexanol, 4-methylpentan-2-ol) in the presence of a suitable catalyst such as a titanium tetraalkoxide and/or sodium alkoxide, and in some cases in the co-presence of a solvent such as hexane or toluene, under appropriate reaction conditions with heating. The transesterification reaction was completed while methanol produced by the reaction was extracted out of the system by distillation or through azeotrope with a reaction solvent under the reaction conditions. The same separation operation as in Reference Example 1 was performed to obtain each of the following α-hydroxyisobutyrate ester. The GC purity of the obtained isobutyric ester is also shown.

n-Propyl α-hydroxyisobutyrate (GC purity: 99.8%)

Isopropyl α-hydroxyisobutyrate (GC purity: 99.6%)

n-Butyl α-hydroxyisobutyrate (GC purity: 99.9%)

Isobutyl α-hydroxyisobutyrate (GC purity: 99.6%)

sec-Butyl α-hydroxyisobutyrate (GC purity: 99.6%)

2-Methylbutyl α-hydroxyisobutyrate (GC purity: 99.9%)

Neopentyl α-hydroxyisobutyrate (GC purity: 99.9%)

2-Methylpentyl α-hydroxyisobutyrate (GC purity: 99.7%)

n-Hexyl α-hydroxyisobutyrate (GC purity: 99.6%)

Cyclopentyl α-hydroxyisobutyrate (GC purity: 99.8%)

Cyclohexyl α-hydroxyisobutyrate (GC purity: 99.6%)

4-Methylpentan-2-yl α-hydroxyisobutyrate (GC purity: 99.8%)

4-Methylpentan-2-yl α-hydroxyisobutyrate

4-Methylpentan-2-yl α-hydroxyisobutyrate had one asymmetric carbon and was obtained as a mixture of the R-form and the S-form. The resulting 4-methylpentan-2-yl α-hydroxyisobutyrate is considered to be a mixture (racemic form) having a mix ratio of the R-form and the S-form of 1:1.

¹H NMR (500 MHz, $CDCl_3$) δ 0.90 (3H, d, J=6.5 Hz), 0.92 (3H, d, J=7.0 Hz), 1.24 (3H, d, J=6.5 Hz), 1.31 (1H, m), 1.41 (3H, s), 1.42 (3H, s), 1.58-1.65 (2H, m), 3.17 (1H, br s), 5.05 (1H, m)

¹³C NMR (125 MHz, $CDCl_3$) δ 20.3, 22.1, 22.9, 24.7, 27.0, 27.1, 44.9, 71.2, 71.8, 177.2

Exact. Mass 189.15338 ($C_{10}H_{20}O_3$, parent peak), 105.05906 ($C_4H_8O_3$)

Example 14: Synthesis of isoamyl α-hydroxyisobutyrate 25.0 g of α-hydroxyisobutyric acid (available from Mitsubishi Gas Chemical Company, Inc.), 105.0 g of isoamyl alcohol (available from Tokyo Chemical Industry Co., Ltd., isomer mixture of 17% 2-methyl butanol and 83% 3-methyl butanol), 25.0 g of hexane (available from Wako Pure Chemical Industries, Ltd.), and 1.3 g of p-toluenesulfonic acid (available from Wako Pure Chemical Industries, Ltd.) were loaded in a 300-mL glass round bottom flask equipped with a condenser, a stirrer, and a Dean-Stark apparatus. An esterification reaction was performed under reflux at normal pressure. The reaction was performed for 4 hours while water produced was azeotroped with hexane and separated by the Dean-Stark apparatus. The catalyst was neutralized with a 10% aqueous solution of sodium hydroxide, and washing was performed twice with a 10% aqueous solution of sodium hydrogen carbonate and twice with a saturated aqueous solution of sodium chloride. Then, distillation was performed under reduced pressure to obtain 19.3 g of isoamyl α-hydroxyisobutyrate (GC purity as isomer mixture of 17% 2-methylbutyl α-hydroxyisobutyrate and 83% 3-methylbutyl α-hydroxyisobutyrate: 99.8%) as the fraction at 19 hPa and 84° C. The reaction formula for this reaction is shown as Formula (7) below.

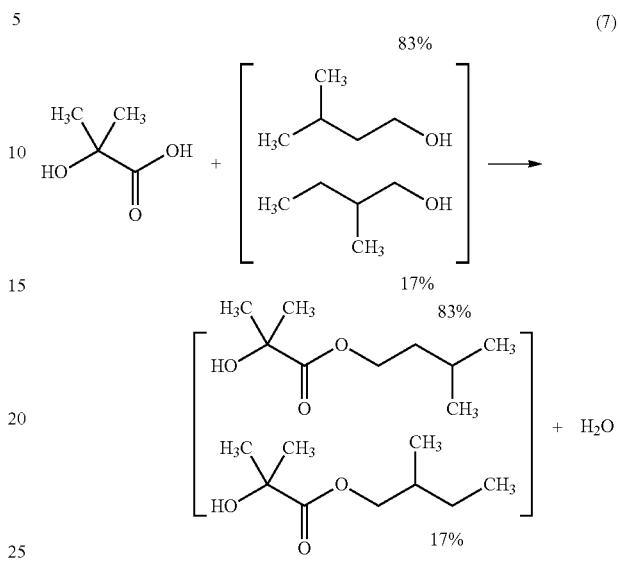

The results of aroma evaluation performed by perfumers for the various α-hydroxyisobutyrate esters obtained by the method described above are shown in Table 1.

TABLE 1

| | Structural formula | Aroma evaluation |
|---|---|---|
| Example 1 | ![structure] | Mint-like aroma<br>Chamomile-like herbal aroma<br>Green apple-like fruity aroma |
| Example 2 | ![structure] | Mint-like aroma<br>Lilac-like white floral aroma<br>Sweet coconut-like aroma |
| Example 3 | ![structure] | Mint-like aroma<br>Lilac-like floral-green aroma |
| Example 4 | ![structure] | Mint-like aroma<br>Floral aroma<br>Coconut-like aroma |
| Example 5 | ![structure] | Mint-like aroma<br>Sweet floral aroma<br>Coconut-like aroma |
| Example 6 | ![structure] | Floral green aroma<br>Balsamic green aroma<br>Fruity-like green aroma |

TABLE 1-continued

| | Structural formula | Aroma evaluation |
|---|---|---|
| Example 7 | [structure: 2-hydroxy-2-methylpropanoate of 3-methylpentyl] | Muguet-like floral aroma<br>Lilac-like floral aroma<br>Green mint-like aroma<br>Coconut-like fruity aroma |
| Example 8 | [structure] | Muguet-like floral aroma<br>Rose-like floral aroma<br>Fresh floral aroma<br>Lilac-like floral aroma<br>Coconut-like fruity aroma |
| Example 9 | [structure] | Peach-like fruity aroma<br>Spicy pear-like aroma<br>Coconut-like fruity aroma<br>Fruity marine aroma |
| Example 10 | [structure] | Sweet milky aroma<br>Floral aroma<br>Strong green aroma |
| Example 11 | [structure: cyclopentyl ester] | Fresh mint-like aroma<br>Fruity aroma<br>Lilac-like, lily of the valley-like, and gardenia-like<br>White floral aroma |
| Example 12 | [structure: cyclohexyl ester] | Mint-like aroma<br>Sweet coconut-like aroma<br>Lilac-like floral aroma |
| Example 13 | [structure] | Green mint-like aroma<br>Spicy aroma<br>Jasmine-like floral aroma<br>Peach-like fruity aroma |
| Example 14 | [structure] 83%<br>[structure] 17% | Mild mint-like aroma<br>Floral aroma<br>Green aldehyde-tone aroma<br>Sweet coconut milk-like aroma |

<Evaluation of Biodegradability and Bioconcentration of Fragrance Materials>

One of methods for evaluating biodegradability of a compound is the OECD test guideline 301 C. In accordance with the method, assessment of biodegradability is possible for the compound from the biochemical oxygen demand and the actual rate of oxygen uptake in an aqueous solution in which the compound and aerobic microorganisms coexist.

Calculation software "Biowin5" and "Biowin6" is known and used in a method for easily and accurately estimating the probability of biodegradation of the compound in compliance with this test method.

In addition, one method for evaluating bioconcentration of compounds is the OECD test guideline 305. In accordance with the method, the degree of concentration can be determined from the amount of a compound incorporated into a fish body when the compound is exposed to the fish. Calculation software "BCFWIN" is known as a method for easily and accurately estimating the degree of bioconcentration of the compound in compliance with this test method.

The software is available to the public as one of modules of calculation software called "The Estimations Programs Interface for Windows version 4.1", created by the United States Environmental Protection Agency (EPA) for the purpose of evaluating the environmental effects of chemical substances, and is used in the compound classification for The Globally Harmonized System of Classification and Labelling of Chemicals (GHS) and the review of new chemical substances by the United States Environmental Protection Agency. This software was used to evaluate the difference in biodegradability and bioconcentration between existing fragrance materials and the compounds according to an embodiment of the present invention.

Menthol, menthone, and carvone were selected as representative examples of existing fragrance materials similar to the compounds according to an embodiment of the present invention having a mint tone, and evaluated along with the compounds according to an embodiment of the present invention. The SMILES formulas used for input to the software and the output results of the probabilities of good degradability by "Biowin5 (linear prediction model)" and "Biowin6 (non-linear prediction model)" are shown in Tables 2 to 3. A larger value of the results indicates better degradability: for a value of 0.5 or more, the compound was rated as having good degradability (symbol "A" in the table), and for a value of less than 0.5, the compound was rated as having low degradability (symbol "B" in the table).

In addition, as evaluation of the bioconcentration by "BCFWIN version 3.01", the output results according to both the "regression-based method" and "Arnot-Gobas method" are shown in Tables 2 to 3. In both the methods, a larger value means concentration from the environment to the fish bodies. Such a value serves as an indicator showing an adverse effect on the environment caused by the food chain.

From Table 2 to Table 3, the results obtained show that the compounds according to an embodiment of the present invention were expected to have good biodegradability and low bioconcentration with respect to menthol, menthone, and carvone, which were the existing fragrance materials similar to the compounds according to an embodiment of the present invention. The results indicated that the compounds according to an embodiment of the present invention are easily biodegraded and unlikely to be bioconcentrated after being released into the environment as fragrances, and thus exhibited a lower impact on the environment.

TABLE 2

| | | | Biodegradability | | | | Bioconcentration (L/kg wet-wt) | |
| --- | --- | --- | --- | --- | --- | --- | --- | --- |
| | | | Biowin5 | | Biowin6 | | BCFWIN | BCFWIN Arnot-Gobas |
| | Structural formula | SMILES | Degradation probability | Score | Degradation probability | Score | regression-based method | method (upper trophic) |
| Example 1 | H$_3$C, CH$_3$ / HO / O / CH$_3$ / O | OC(C)(C)C(OCC)=O | 0.781 | A | 0.885 | A | 3.16 | 0.94 |
| Example 2 | H$_3$C, CH$_3$ / HO / O / CH$_3$ / O | OC(C)(C)C(OCCC)=O | 0.789 | A | 0.888 | A | 3.16 | 1.08 |
| Example 3 | H$_3$C, CH$_3$ / HO / O / CH$_3$ / O / CH$_3$ | OC(C)(C)C(OC(C)C)=O | 0.640 | A | 0.756 | A | 3.16 | 1.04 |
| Example 4 | H$_3$C, CH$_3$ / HO / O / CH$_3$ / O | OC(C)(C)C(OCCCC)=O | 0.796 | A | 0.890 | A | 3.12 | 1.58 |
| Example 5 | H$_3$C, CH$_3$ / HO / O / CH$_3$ / CH$_3$ / O | OC(C)(C)C(OCC(C)C)=O | 0.647 | A | 0.760 | A | 2.79 | 1.44 |
| Example 6 | H$_3$C, CH$_3$ / HO / O / CH$_3$ / O / CH$_3$ | OC(C)(C)C(OC(C)CC)=O | 0.647 | A | 0.760 | A | 2.79 | 1.44 |

TABLE 2-continued

| | Structural formula | SMILES | Biodegradability | | | | Bioconcentration (L/kg wet-wt) | |
|---|---|---|---|---|---|---|---|---|
| | | | Biowin5 | | Biowin6 | | BCFWIN regression-based method | BCFWIN Arnot-Gobas method (upper trophic) |
| | | | Degradation probability | Score | Degradation probability | Score | | |
| Example 7 | | OC(C)(C)C(OCC(C)CC)=O | 0.655 | A | 0.765 | A | 5.87 | 2.68 |
| Example 8 | | OC(C)(C)C(OCC(C)(C)C)=O | 0.724 | A | 0.780 | A | 5.55 | 2.81 |
| Example 9 | | OC(C)(C)C(OCC(C)CCC)=O | 0.663 | A | 0.769 | A | 12.39 | 5.75 |
| Example 10 | | OC(C)(C)C(OCCCCCC)=O | 0.812 | A | 0.895 | A | 13.87 | 6.71 |
| Example 11 | | OC(C)(C)C(OC1CCCC1)=O | 0.703 | A | 0.778 | A | 4.95 | 2.38 |
| Example 12 | | OC(C)(C)C(OC1CCCCC1)=O | 0.681 | A | 0.748 | A | 10.45 | 5.64 |

TABLE 3

| | Structural formula | SMILES | Biodegradability | | | | Bioconcentration (L/kg wet-wt) | |
|---|---|---|---|---|---|---|---|---|
| | | | Biowin5 | | Biowin6 | | BCFWIN regression-based method | BCFWIN Arnot-Gobas method (upper trophic) |
| | | | Degradation probability | Score | Degradation probability | Score | | |
| Example 13 | | OC(C)(C)C(OC(C)CC(C)C)=O | 0.514 | A | 0.565 | A | 11.09 | 5.16 |
| Example 14 | | OC(C)(C)C(OCCC(C)C)=O | 0.655 | A | 0.765 | A | 5.87 | 2.68 |

TABLE 3-continued

| | Structural formula | SMILES | Biodegradability | | | | Bioconcentration (L/kg wet-wt) | |
| --- | --- | --- | --- | --- | --- | --- | --- | --- |
| | | | Biowin5 | | Biowin6 | | BCFWIN regression-based method | BCFWIN Arnot-Gobas method (upper trophic) |
| | | | Degradation probability | Score | Degradation probability | Score | | |
| | 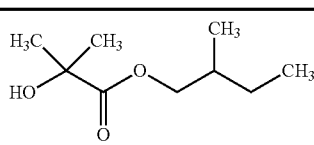 | OC(C)(C)C(OCC(C)CC)=O | 0.655 | A | 0.765 | A | 5.87 | 2.68 |
| Comparative Example 1 | 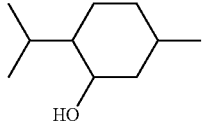<br>(Menthol) | CC(C)C1CCC(C)CC1O | 0.455 | B | 0.331 | B | 59.16 | 23.33 |
| Comparative Example 2 | 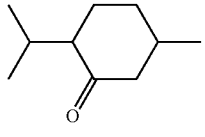<br>(Menthone) | CC(C)C1CCC(C)CC1=O | 0.406 | B | 0.335 | B | 47.75 | 74.13 |
| Comparative Example 3 | 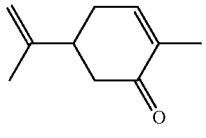<br>(Carvone) | C=C(C)C(C1)CC=C(C)C1=O | 0.454 | B | 0.375 | B | 28.51 | 43.35 |

Example 15: White Floral-Type Fragrance Composition

A fragrance composition was prepared by adding 21.3 parts by mass of the isopropyl α-hydroxyisobutyrate obtained in Example 3 to 78.7 parts by mass of a fragrance composition having a composition shown in Table 4.

According to the aroma evaluation by perfumers, addition of the isopropyl α-hydroxyisobutyrate of Example 3 to the fragrance composition having the composition described in Table 4 enabled to impart floral green having a crisp, fresh, and light feeling. As a result, provided was a novel white floral-type fragrance composition to which a mint-like and lilac-like floral green aroma was imparted. The aroma of this fragrance composition seems to be suitable for perfuming skin lotion, deodorant sheets, body powder, and the like.

TABLE 4

| Blend ingredients | parts by mass |
| --- | --- |
| Benzyl acetate | 22.8 |
| D-Limonene | 17.7 |
| trans-tert-Butyl cyclohexanol | 10.5 |
| Linalool | 9.1 |
| Sandalwood oil (10%) | 8.1 |

TABLE 4-continued

| Blend ingredients | parts by mass |
| --- | --- |
| 2-Phenylethyl alcohol | 5.4 |
| Methyl dihydrojasmonate | 5.1 |
| Total | 78.7 |

* Blend ingredients in parentheses in the table were used as a solution diluted with dipropylene glycol. The figures represents mass % of the fragrance included in the solution.

Example 16: Mint-type Fragrance Composition

A fragrance composition was prepared by adding 90 parts by mass of the isopropyl α-hydroxyisobutyrate obtained in Example 3 to 10 parts by mass of L-menthol. In addition, a fragrance composition was prepared, as a comparative target, by adding 90 parts by mass of 99.5% ethanol to 10 parts by mass of L-menthol. According to the aroma evaluation by perfumers, the difference between both the aromas were comparatively evaluated. DL-menthone and L-carvone were also comparatively evaluated in the same manner. The results of the comparative evaluation of the aromas were summarized in Table 5.

Typical mint-tone fragrance ingredients such as L-menthol, DL-menthone, and L-carvone, when diluted with mint-tone isopropyl α-hydroxyisobutyrate, were strongly lifted up and had improved diffusivity with no impediment to the mint tone of L-menthol, DL-menthone, and L-carvone, and a refreshing feeling of mint was more strongly felt. Simultaneously, a floral and green feeling was also added to thereby provide a more natural mint-like aroma. The isopropyl α-hydroxyisobutyrate obtained in Example 3 was useful as an ingredient for lifting up mint-tone fragrance ingredients.

TABLE 5

| | Aroma evaluation of solution of ester of Example 3 in comparison with ethanol solution |
|---|---|
| L-Menthol | A more natural mint-like aroma having an emphasized refreshing feeling and emphasized diffusivity, to which a green nuance having freshness and a floral feeling having faint sweetness were imparted, in comparison with an ethanol solution. |
| DL-Menthone | A more natural mint-like aroma having an emphasized refreshing feeling and emphasized diffusivity, to which a green nuance having freshness was imparted, in comparison with an ethanol solution. |
| L-Carvone | A more natural and mild mint-like aroma, to which a soft green nuance and a floral feeling having faint sweetness were imparted, in comparison with an ethanol solution. |

Example 17: Gardenia-Type Fragrance Composition

A fragrance composition was prepared by adding 15.7 parts by mass of n-butyl α-hydroxyisobutyrate obtained in Example 4 to 84.3 parts by mass of a fragrance composition having a composition shown in Table 6.

According to the aroma evaluation by perfumers, addition of the n-butyl α-hydroxyisobutyrate of Example 4 to the fragrance composition having the composition described in Table 6 enabled to enhance the sweetness specific to gardenia and impart brisk green. As a result, provided was a novel gardenia-type fragrance composition having enhanced milky sweetness, to which a green tone was imparted. The aroma of this fragrance composition seems to be suitable for perfuming hair treatment, milky lotion, skin cream, body lotion, and the like.

TABLE 6

| Blend ingredients | parts by mass |
|---|---|
| a-Hexyl cinnamyl aldehyde | 21.1 |
| a-Terpineol | 13.4 |
| δ-Decanolactone | 10.9 |
| Coumarin (10%) | 9.2 |
| Benzyl acetate | 6.5 |
| 2-Phenylethyl alcohol | 5.6 |
| Methyl dihydrojasmonate | 5.5 |
| Linalool | 4.9 |
| Hydroxycitronellal | 4.5 |
| Styralyl acetate | 1.5 |
| Indole (1%) | 1.1 |
| Total | 84.3 |

* Blend ingredients in parentheses in the table were used as a solution diluted with dipropylene glycol. The figures represents mass % of the fragrance included in the solution.

Example 18: Muguet-Type Fragrance Composition

A fragrance composition was prepared by adding 16.4 parts by mass of the isobutyl α-hydroxyisobutyrate obtained in Example 5 to 83.6 parts by mass of a fragrance composition having a composition shown in Table 7.

According to the aroma evaluation by perfumers, addition of the isobutyl α-hydroxyisobutyrate of Example 5 to the fragrance composition having the composition described in Table 7 provided an elegant novel muguet-type fragrance composition having sweetness with an enhanced woody tone, to which a brisk green tone was imparted. The aroma of this fragrance composition seems to be suitable for perfuming shampoo, body soap, and facial foam, and the like.

TABLE 7

| Blend ingredients | parts by mass |
|---|---|
| Methyl dihydrojasmonate | 33.2 |
| Cyclopentadecanone | 25.3 |
| Benzyl acetate | 9.2 |
| Hydroxycitronellal | 8.1 |
| 2-Phenylethyl alcohol | 4.0 |
| Bergamot oil (10%) | 3.8 |
| Total | 83.6 |

* Blend ingredients in parentheses in the table were used as a solution diluted with dipropylene glycol. The figures represent mass % of the fragrance included in the solution.

Example 19: Orange Osmanthus-Type Fragrance Composition

A fragrance composition was prepared by adding 15.2 parts by mass of the isobutyl α-hydroxyisobutyrate obtained in Example 5 to 84.8 parts by mass of a fragrance composition having a composition shown in Table 8.

According to the aroma evaluation by perfumers, addition of the isobutyl α-hydroxyisobutyrate of Example 5 to the fragrance composition having the composition described in Table 8 provided a novel orange osmanthus-type fragrance composition having sharp and warm sweetness with milky sweetness and a woody tone emphasized, to which a brisk green tone was imparted. The aroma of this fragrance composition seems to be suitable for perfuming body lotion, hand cream, and the like.

TABLE 8

| Blend ingredients | parts by mass |
|---|---|
| Methyl dihydrojasmonate | 30.3 |
| Cyclopentadecanone | 23.1 |
| Benzyl acetate | 8.6 |
| Hydroxycitronellal | 7.8 |
| γ-Undecalactone (C-14) | 7.2 |
| 2-Phenylethyl alcohol | 4.0 |
| Bergamot oil (10%) | 3.6 |
| Total | 84.8 |

* Blend ingredients in parentheses in the table were used as a solution diluted with dipropylene glycol. The figures represent mass % of the fragrance included in the solution.

Example 20: Jasmine-Type Fragrance Composition

A fragrance composition was prepared by adding 19.5 parts by mass of the 4-methylpentan-2-yl α-hydroxyisobutyrate obtained in Example 13 to 80.5 parts by mass of a fragrance composition having a composition shown in Table 9.

According to the aroma evaluation by perfumers, addition of the 4-methylpentan-2-yl α-hydroxyisobutyrate of Example 13 to the fragrance composition having the composition described in Table 9 provided the entire integrity and improved the balance. As a result, provided was a novel jasmine-type fragrance composition being natural and having gorgeousness, to which spicy warmth and fruity sweetness were imparted. The aroma of this fragrance composition seems to be suitable for perfuming skin cream, soap, hair mousse, and the like.

TABLE 9

| Blend ingredients | parts by mass |
|---|---|
| Benzyl acetate | 20.4 |
| Citronellol | 11.8 |
| 2-Phenylethyl alcohol | 8.8 |
| a-Hexyl cinnamaldehyde | 8.2 |
| Geraniol | 7.9 |
| Linalool | 7.8 |
| Benzyl alcohol | 5.2 |
| D-Limonene | 4.1 |
| Coumarin (10%) | 3.8 |
| Eugenol | 2.5 |
| Total | 80.5 |

* Blend ingredients in parentheses in the table were used as a solution diluted with dipropylene glycol. The figures represent mass % of the fragrance included in the solution.

INDUSTRIAL APPLICABILITY

An α-hydroxyisobutyrate ester compound according to an embodiment of the present invention has an excellent aroma and is expected to be used itself as a fragrance. Additionally, use of the compound as a fragrance ingredient can provide a fragrance composition excellent in aroma properties. The composition, when blended in a variety of products, exhibits desired perfuming properties.

Furthermore, it was shown that the compounds obtained in Examples each have excellent biodegradability, low bioconcentration, and a low impact on the environment and are suitable for use.

The invention claimed is:

1. A fragrance composition, comprising a compound represented by the following formula (1) as an active ingredient:

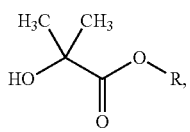

(1)

wherein R is selected from the group consisting of a sec-butyl group, a 2-methylbutyl group, a 3-methylbutyl group, a neopentyl group, a 2-methylpentyl group, 4-methylpentan-2-yl group, a n-hexyl group, a cyclopentyl group, and a cyclohexyl group.

2. A compound, represented by the following formula (2):

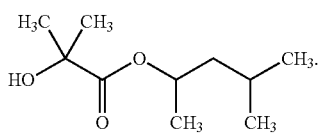

(2)

3. The fragrance composition of claim 1, comprising from 0.001 to 90 mass % of the compound represented by the formula (1).

* * * * *